(12) United States Patent
Lussier et al.

(10) Patent No.: US 7,918,811 B2
(45) Date of Patent: Apr. 5, 2011

(54) SUPPORT DEVICE FOR A JOINT

(75) Inventors: Michel Lussier, Portland, OR (US);
Brook Dion Athay, Portland, OR (US);
John Whiteman, Nürnberg (DE);
Albert Gollhofer, Stegen (DE)

(73) Assignee: adidas International Marketing B.V., Amsterdam (NL)

( * ) Notice: Subject to any disclaimer, the term of this patent is extended or adjusted under 35 U.S.C. 154(b) by 289 days.

(21) Appl. No.: 12/186,049

(22) Filed: Aug. 5, 2008

(65) Prior Publication Data
US 2010/0036306 A1    Feb. 11, 2010

(51) Int. Cl.
*A61F 5/00*    (2006.01)
(52) U.S. Cl. ............................ 602/23; 602/27
(58) Field of Classification Search .............. 602/23–29, 602/60–62; 128/882
See application file for complete search history.

(56) References Cited

U.S. PATENT DOCUMENTS

| | | |
|---|---|---|
| 4,571,856 A | 2/1986 | Lin et al. |
| 4,727,863 A | 3/1988 | Nelson |
| 4,878,504 A | 11/1989 | Nelson |
| 4,989,350 A | 2/1991 | Bunch et al. |
| 5,016,623 A | 5/1991 | Krahenbuhl |
| 5,092,319 A | 3/1992 | Grim |
| 5,109,613 A | 5/1992 | Van Dyke |
| 5,317,820 A | 6/1994 | Bell et al. |
| 5,379,530 A | 1/1995 | Bell et al. |
| 5,400,529 A | 3/1995 | Bell et al. |
| 5,430,960 A | 7/1995 | Richardson |
| 5,678,330 A * | 10/1997 | Van Dyke et al. ............ 36/89 |
| 5,741,222 A | 4/1998 | Fiore |
| 5,865,778 A * | 2/1999 | Johnson ...................... 602/27 |
| 5,896,683 A | 4/1999 | Foxen et al. |
| 6,022,332 A | 2/2000 | Nelson |
| 6,024,712 A | 2/2000 | Iglesias et al. |
| 6,228,043 B1 | 5/2001 | Townsend et al. |
| 6,270,468 B1 | 8/2001 | Townsend et al. |
| 6,682,497 B2 * | 1/2004 | Jensen et al. ................. 602/27 |
| 6,692,454 B1 | 2/2004 | Townsend et al. |
| 6,715,218 B2 | 4/2004 | Johnson |
| 6,718,656 B2 | 4/2004 | Houser et al. |
| 7,171,766 B2 | 2/2007 | Bouche et al. |
| 7,243,444 B2 | 7/2007 | Selner |
| 2003/0083603 A1 | 5/2003 | Nelson |
| 2004/0019309 A1 | 1/2004 | Nelson et al. |
| 2004/0033874 A1* | 2/2004 | Elbaz et al. ................. 482/148 |
| 2005/0268493 A1 | 12/2005 | Foxen et al. |
| 2006/0137226 A1 | 6/2006 | Jung et al. |
| 2007/0213649 A1 | 9/2007 | Gaylord et al. |

* cited by examiner

*Primary Examiner* — Michael A. Brown
(74) *Attorney, Agent, or Firm* — Sterne, Kessler, Goldstein & Fox P.L.L.C.

(57) ABSTRACT

Support devices for joints of the human body are disclosed. A support device for an ankle includes a main body having a medial portion and a lateral portion disposed about the ankle, and an interior surface; at least one of a medial support member disposed in a cavity in the medial portion of said main body and a lateral support member disposed in a cavity in the lateral portion of said main body; a strap disposed on a proximal portion of said main body, said strap having fastening means adapted to create a first level of pressure in the front of the lower leg immediately proximal to the ankle and a second level of pressure in the rear of the lower leg immediately proximal to the ankle; and one or more proprioceptive members disposed on the interior surface of said main body.

25 Claims, 9 Drawing Sheets

SUPPORT DEVICE FOR A JOINT

FIELD OF THE INVENTION

The present invention relates generally to support devices, and more particularly to support devices for joints of the human body.

BACKGROUND OF THE INVENTION

Athletic maneuvers can create extreme forces in the various joints of the human body, including, but not limited to, the ankle, knee, elbow, or wrist. For example, the rapid lateral movements made by basketball or tennis players often results in extreme forces being transmitted throughout a player's shoe, foot, and ankle. Depending on the direction of the movement, these forces may result in excessive ankle inversion, wherein the sole of the shoe rolls inward toward the medial plane, or excessive ankle eversion, wherein the sole of the shoe rolls outward toward a lateral plane.

The joints of the human body and their surrounding anatomy are also subjected to extreme forces in contact sports. For example, a football player's wrists and knees may be exposed to extreme forces when blocking or being tackled by an opponent. Depending on the nature of the impact, these forces could result in painful hyperextensions, hyperflexions, or a variety of other joint injuries.

Regardless of the sport being played or the particular cause of the injury, temporary undesirable displacement of the body's joints can cause traumatic damage to them. The risk of such undesirable displacement and the resulting injury can be greatly reduced by partially restricting the motion of the joint and its surrounding anatomy, and shielding them from external impact. Known methods for attempting to reduce the aforementioned risk include taping or wrapping the joint or positioning a highly rigid support device about the joint.

Taping or wrapping the joint of an athlete in elastic bands can be a time-consuming and relatively expensive procedure, which generally can not be performed by the athlete. The taping or wrapping typically needs to be done by an athletic trainer or other person with specialized knowledge to properly and effectively secure the joint. In some cases, simple tapes and bands may not be truly effective at controlling motion, and may often serve as little more than a psychological crutch for athletes. Moreover, these devices do little to shield the joint surface from external impacts and tapes tend to weaken after only a few minutes of use.

When more rigid support devices are used, stiff support members are typically coupled with flexible sleeves and/or simple straps. Such devices, while potentially offering somewhat improved stability over tapes or bands, are often uncomfortable and add too much extra weight. Moreover, such devices often restrict the natural range of motion of the joint in certain directions to an extent that athletic performance is compromised or impeded. Furthermore, the geometry and placement of the rigid members of these devices often tend to exacerbate, rather than mitigate, the effects of external impact forces imparted to the joint or surrounding anatomy.

The joint support devices described so far aim to provide only mechanical immobilization of a joint and its surrounding body structures. More advanced joint support devices may incorporate means to stimulate the body itself to contribute to the joint supporting effort. Some joint support devices have incorporated elements intended to stimulate the body's proprioceptive response, which is activated via receptors located in muscles, tendons, ligaments, and joint capsule areas.

Proprioceptive receptors are capable of initiating appropriate tension in their associated muscles after sensing relative motion between, or other tactile sensations on, portions of the skin in the vicinity of these receptors. In order to increase the sensitivity for activating these receptors while wearing a joint support device, elements having a relatively high coefficient of friction relative to the skin can be placed on an interior surface of the support device in contact with the skin. Because of these highly frictional elements, perturbations of the surrounding support device due to joint movements are more likely to be transmitted directly to the surface of the skin around the joint to be supported. The precise location of these highly frictional elements determines which receptors will be activated (and, thus, which muscles will be tensed). Thus, the proprioceptive response could be used to initiate quicker muscular reactions that will aid in resisting—or at least slowing the rate of—undesirable joint displacement.

Known methods of incorporating proprioceptive members into joint support devices have many shortcomings. Often, the proprioceptive members are paired with other structural elements that make the support device too cumbersome to wear while participating in a competitive sport. In addition, the main body of the joint support device housing the proprioceptive members may not be capable of protecting the wearer from further injury. Furthermore, many proprioceptive members are not placed in anatomical locations that will maximize the body's ability to resist the unwanted motion.

Accordingly, a need exists for joint support devices that are capable of overcoming one or more of the limitations described above.

BRIEF SUMMARY OF THE INVENTION

Embodiments of the present invention may relate to a support device for an ankle which may include a main body having a medial portion and a lateral portion disposed about the ankle, and an interior surface; at least one of a medial support member disposed in a cavity in the medial portion of said main body and a lateral support member disposed in a cavity in the lateral portion of said main body; a strap disposed on a proximal portion of said main body, said strap having fastening means adapted to create a first level of pressure in the front of the lower leg immediately proximal to the ankle and a second level of pressure in the rear of the lower leg immediately proximal to the ankle; and one or more proprioceptive members disposed on the interior surface of said main body.

Embodiments of the present invention may also relate to a support device for an ankle which may include a main body having a medial portion and a lateral portion disposed about the ankle, and an interior surface; at least one of a medial support member disposed in a cavity in the medial portion of said main body and a lateral support member disposed in a cavity in the lateral portion of said main body; a strap disposed on a proximal portion of said main body; and proprioceptive members disposed on a medial portion of the interior surface of said main body above the ankle and on a lateral portion of the interior surface of said main body above the ankle.

Embodiments of the present invention may further relate to an article of footwear having an integrated support device for an ankle which may include an upper having a medial portion and a lateral portion disposed about the ankle; a sole disposed below said upper; at least one of a medial support member disposed in a cavity in the medial portion of said upper and a lateral support member disposed in a cavity in the lateral portion of said upper; a strap disposed on a proximal portion of said upper; and one or more proprioceptive members disposed on an interior surface of said upper.

Embodiments of the present invention may also relate to a support device for an ankle which may include a main body having an interior surface, said main body including a medial portion having a medial cavity formed therein, a lateral portion having a lateral cavity formed therein, and a tab extending from the lateral portion, said tab having fastening means disposed on an interior surface and an exterior surface of the tab; a medial support member disposed in the medial cavity; a lateral support member disposed in the lateral cavity; a strap having a fixed end attached to the medial portion of said main body and a free end, and having exterior fastening means disposed on an exterior surface of said strap at the fixed end and interior fastening means disposed on an interior surface at the free end, wherein the interior tab fastening means is operatively connected to the exterior strap fastening means, and the exterior tab fastening means is operatively connected to the interior strap fastening means; and proprioceptive members disposed on a medial portion of the interior surface of said main body above the ankle and a lateral portion of the interior surface of said main body above the ankle. Further embodiments, features, and advantages of the present invention, as well as the structure and operation of the various embodiments of the present invention, are described in detail below with reference to the accompanying drawings.

BRIEF DESCRIPTION OF THE FIGURES

The accompanying figures, which are incorporated herein and form a part of the specification, illustrate several embodiments of the present invention by way of example, and not by way of limitation, and, together with the description, further serve to explain the principles of the invention and to enable a person skilled in the pertinent art to make and use the invention.

To the extent that only a right or left joint support device is described for a particular embodiment of the present invention, it will be apparent to one of ordinary skill in the art that a support device suitable for the corresponding joint on the opposite side of the body, though not specifically described, may comprise a mirror image of the described support device.

FIG. 6(*a*) is a front view of a first support member according to an embodiment of the present invention.

FIG. 6(*b*) is a side view of the first support member shown in FIG. 6(*a*) according to an embodiment of the present invention.

FIG. 8(*a*) is an interior view of a strap which has been removed from a main body of a joint support device according to an embodiment of the present invention.

FIG. 8(*b*) is an exterior view of a strap which has been removed from a main body of a joint support device according to an embodiment of the present invention.

DETAILED DESCRIPTION OF THE INVENTION

The present invention will now be described in detail with reference to embodiments thereof as illustrated in the accompanying drawings. While specific configurations and arrangements are discussed, it should be understood that this is done for illustrative purposes only. References to "an embodiment", "one embodiment", "another embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, a person skilled in the relevant art will recognize that other configurations and arrangements can be used without departing from the spirit and scope of the invention.

A support device 10 for a joint according to an embodiment of the present invention may include a main body 100 disposed around the joint. A first cavity 211 containing a first support member 203 may be disposed in a first portion 124 of the main body 100. A second cavity 213 containing a second support member 205 may be disposed opposite of the first cavity 211 in a second portion 126 of the main body 100. A strap 300 may be disposed on a proximal portion 101 of the main body 100, and one or more proprioceptive members 400 may be disposed on interior surfaces 108 of the main body 100.

Embodiments of the support device 10 of the present invention may be used to support various joints of the human body. An example of a support device 10 specifically designed to accommodate an ankle joint is shown generally in FIGS. 1-5. However, it is contemplated that a support device 10 for use with one or more other joints including, but not limited to, the knee, hip, elbow, or wrist is considered to be within the scope and spirit of the present invention.

In one embodiment of the present invention, as shown in FIGS. 1-4, the main body 100 may take the form of a sleeve. However, it is contemplated that other suitable structures capable of generally accommodating the shape of the underlying joint, including, but not limited to, a sheet, capsule, glove, or article of footwear, may be used.

The main body 100 may be constructed out of a single material or multiple materials. Different materials may be joined in layers one on top of the other, or materials may be joined edge-to-edge in a patchwork arrangement by various means including, but not limited to, stitching or gluing. Suitable materials for construction of the main body 100 include, but are not limited to, various natural or synthetic fabrics, leathers, plastics, or rubbers. Portions of main body 100 where more flexibility is desired may incorporate relatively flexible fabrics or materials, whereas portions of main body 100 where more stiffness is desired may incorporate less flexible fabrics or materials.

Figure 3:
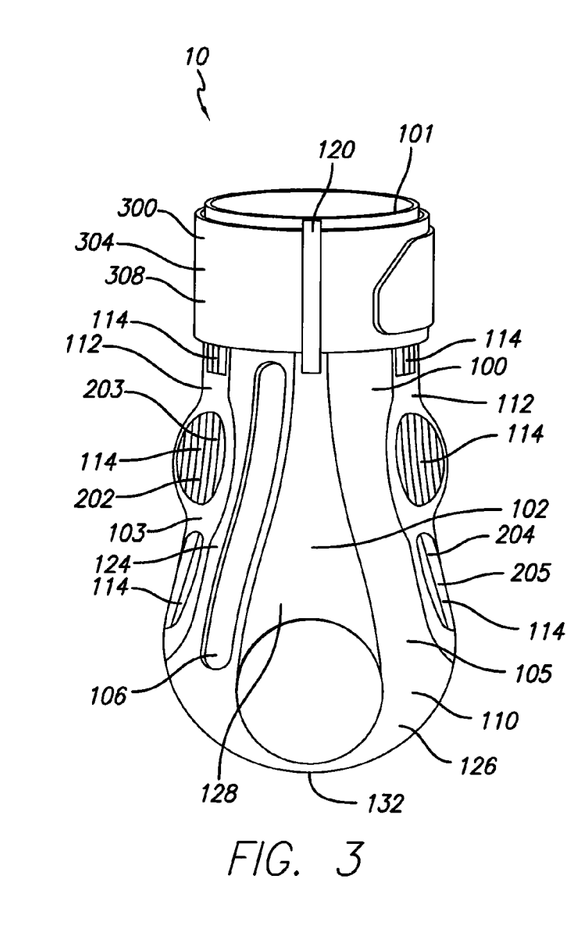
FIG. 3 is a rear view of a support device for an ankle according to an embodiment of the present invention.
Figure 4:
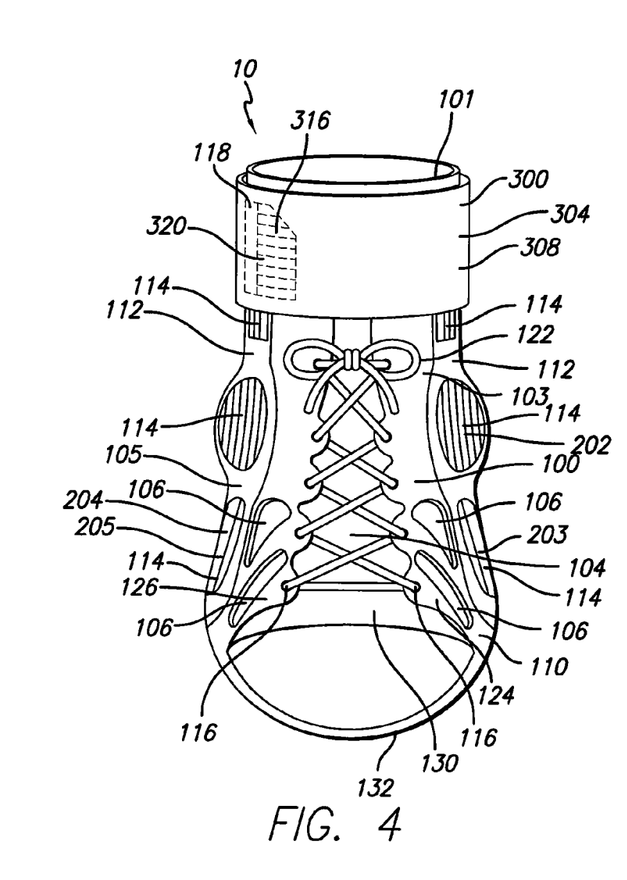
FIG. 4 is a front view of a support device for an ankle according to an embodiment of the present invention.

In one embodiment of the present invention, as shown in FIGS. 3 and 4, the main body 100 may include first and second portions 124 and 126 disposed opposite one another. In one embodiment of the present invention, the first and second portions 124 and 126 comprise a material that is less flexible relative to the other portions of the main body 100. Edges of the first and second portions 124 and 126 may be joined to edges of more flexible third and fourth portions 128 and 130, which may also be also arranged opposite of one another, so as to form the main body 100 of the joint support device 10.

In this configuration, constrained range of motion of the underlying joint in one direction may be achieved, while still allowing for relative freedom of movement in another direction.

In embodiments of the support device 10 adapted for an ankle, as shown in FIGS. 1-4, a medial portion 103 (corresponding to a first portion 124) and the lateral portion 105 (corresponding to the second portion 126) may be arranged opposite of one another across the ankle joint. The medial portion 103 and the lateral portion 105 may be less flexible relative to other portions of the main body 100. A rear portion 102 (corresponding to the third portion 128) and a front portion 104 (corresponding to the fourth portion 130) may also be arranged opposite of one another across the ankle joint, so that edges of the medial, lateral, rear, and front portions 103, 105, 102, and 104 are joined together to form main body 100, as shown in FIGS. 1-4. The rear portion 102 and the front portion 104 may be more flexible than the medial portion 103 and the lateral portion 105. This arrangement may be useful when preventing inversion and eversion ankle injuries where it is desirable to slow ankle roll rates, yet relatively uninhibited ankle flexion and extension are necessary for performance of athletic motions such as running or jumping. For example, a basketball or tennis player may benefit from wearing an ankle brace incorporating such features.

In one embodiment, as shown in FIGS. 1-5, the main body 100 may further comprise a lower portion 132 which wraps underneath the bottom of the foot. The lower portion 132 may be integral with the medial and lateral portions 103 and 105, or the lower portion 132 may be a separate piece of material whose edges are joined to medial and lateral portions 103 and 105. The lower portion 132 in a support device 10 for an ankle may also help to restrict the motion of a joint in a particular direction. For example, the lower portion 132 of a support device 10 for an ankle may be located underfoot towards the heel region, at least partially under the calcaneus bone, so as to create upward compression and close the natural gap in the ankle joint when the foot is not bearing weight. In some embodiments, this configuration may be adapted to help to prevent a variety of unwanted ankle displacements.

Figure 1:
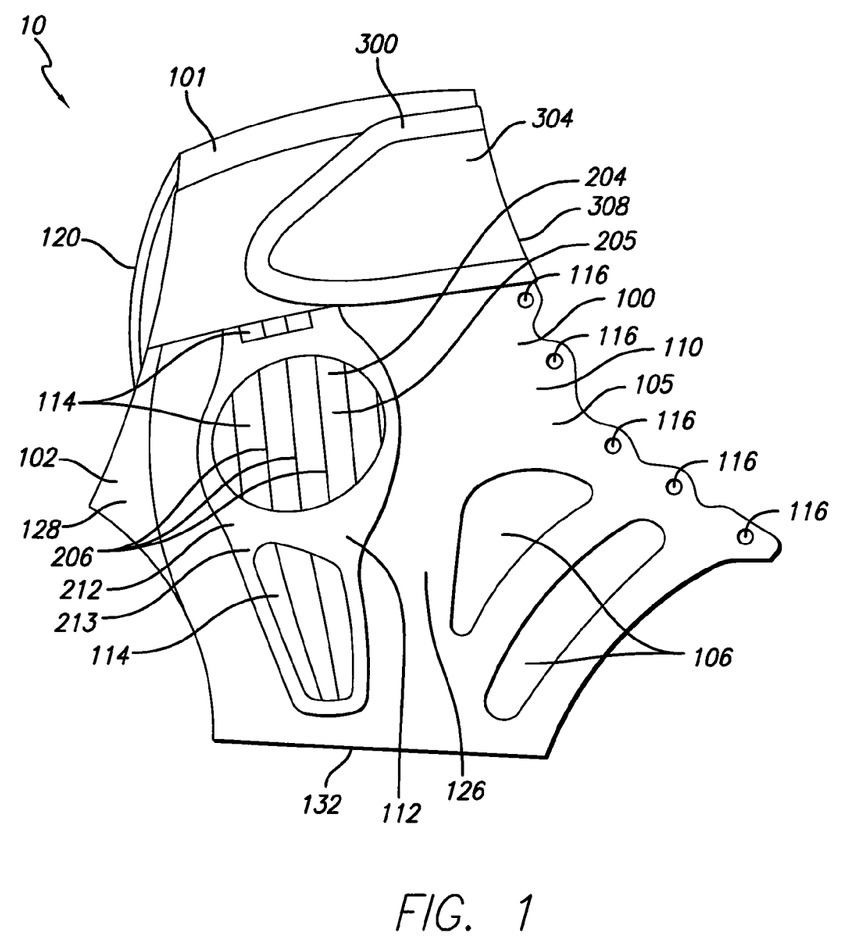
FIG. 1 is a lateral view of a support device for an ankle according to an embodiment of the present invention.
Figure 2:
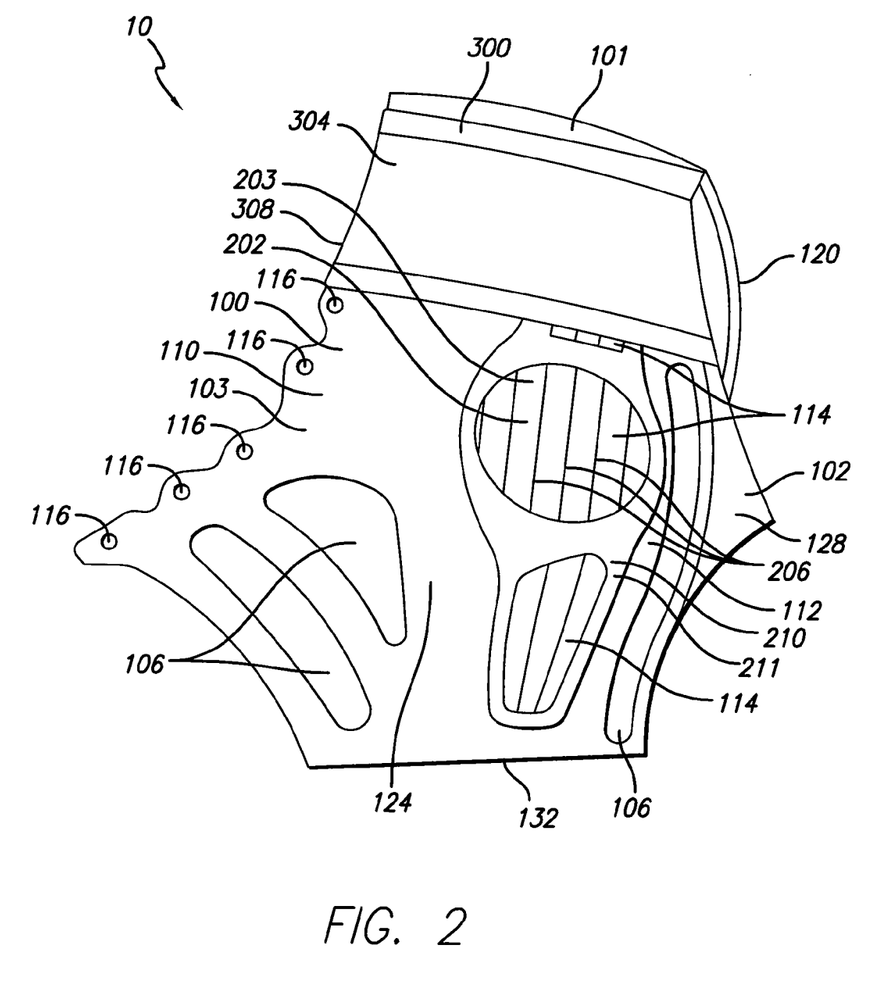
FIG. 2 is a medial view of a support device for an ankle according to an embodiment of the present invention.

In one embodiment of the present invention, as best illustrated by FIGS. 1 and 2, the support device 10 may include localized expandable portions 106 within the bounds of other relatively stiff portions of the main body 100, such as first and second portions 124 and 126. Because the expandable portions 106 may provide localized flexibility of the main body 100, the expandable portions 106 may provide a better fit to a particular wearer's joint and surrounding anatomy, and allow for more joint movement in desirable directions.

In one embodiment of the present invention, the expandable portions 106 may be made of an elastic synthetic layer coated with thin bands of thermoplastic urethane (TPU). However, it is contemplated that other suitable materials which are more flexible than the relatively stiffer portions of the main body 100, such as first and second portions 124 and 126, may be used. In one embodiment, the expandable portions may comprise a lightweight material that may reduce the overall weight of the joint support device 10, or a material that allows for breathability of the skin of the underlying joint and surrounding anatomy. The size, color, and shape of the expandable portions 106 also may be varied to contribute to the overall aesthetics of the support device 10. Furthermore, a single expandable portion 106 or a plurality of expandable portions 106 may be included in the main body 100.

When coupled to a main body 100, first and second support members 203 and 205 may function to prevent a joint from unwanted displacement by providing mechanical resistance against movement in a particular direction. First and second support members 203 and 205 may also serve to shield a joint from impact by, for example, dispersing the forces generated by a localized impact throughout the surface of the support member 203 or 205.

Figure 6A:
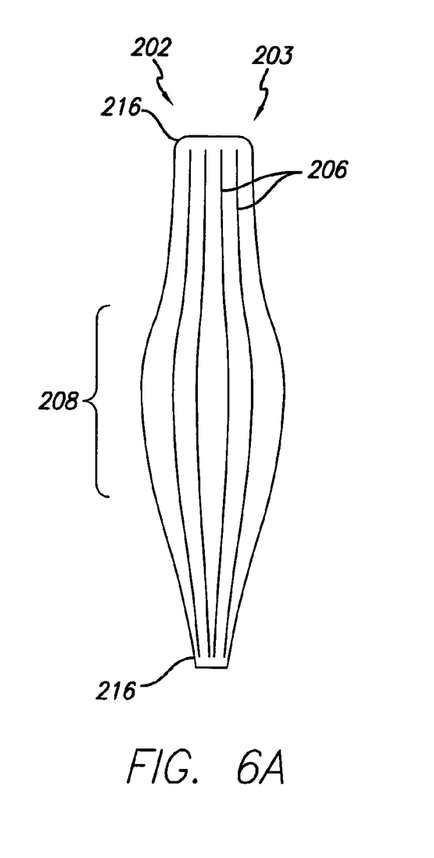
Figure 6B:
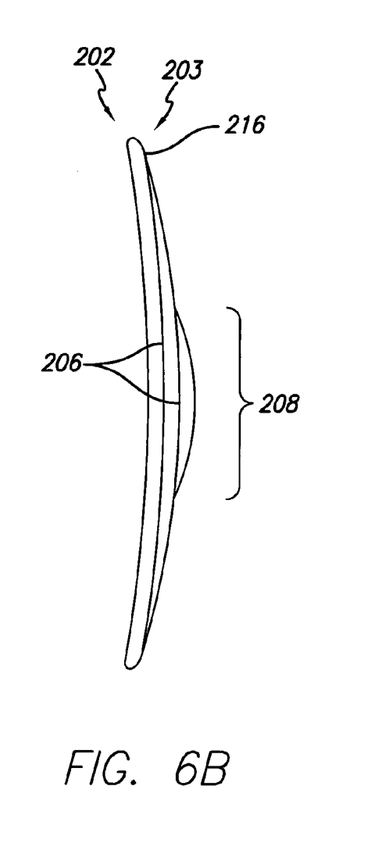

A first support member 203, as best illustrated by FIGS. 6(a) and 6(b), may be housed by a first cavity 211 formed in the first portion 124 of the main body 100. A second support member 205 may be housed by a second cavity 213 formed opposite of the first cavity 211 in the second portion 126 of the main body 100. In one embodiment of the present invention, first and second portions 124 and 126 comprise the relatively stiffer portions of main body 100 described above. The desired locations of first support member 203 and second support member 205 will vary depending on the anatomy of the particular joint and the particular type of displacement and/or injury that is desired to be avoided.

In embodiments of the support device 10 designed primarily to reduce inversion and eversion injuries in an ankle, as shown in FIGS. 1-4, one of first and second support members 203 and 205 may be located in a medial portion 103 of main body 100 near the medial malleolus of the ankle, while the other support member may be located in a lateral portion 105 of main body 100 near the lateral malleolus of the ankle.

In embodiments adapted primarily to reduce excessive radial-ulnar deviations in the wrist, first and second support members 203 and 205 may be located in medial and lateral positions. In embodiments of a wrist support adapted to reduce excessive flexion and extension of the wrist, first and second support members 203 and 205 may be located in dorsal and ventral (or palmar) positions.

The first and second support members 203 and 205 may be made from any number of suitable materials, including, but not limited to, plastics, metals, composites, or combinations thereof. In one embodiment of the present invention, first and second support members 203 and 205 may be formed by injection molding polyethylene or similar material such as, for example, polyamide, polyether block amide, and/or TPU. Whichever material is used, it may be desirable that first and second support members 203 and 205 be rigid enough to prevent excessive joint displacement and mitigate external impact forces, yet flexible enough to allow for flexibility in the desired directions. In this manner, the support device 10 may provide joint protection while allowing a relatively normal freedom of motion required for a particular activity.

First and second support members 203 and 205 may be formed in a variety of different shapes and sizes, depending on the anatomy of the particular joint and the particular type of joint displacement and/or injury that is desired to be avoided. Generally, first and second support members 203 and 205 are designed to accommodate the shape of the joint to be supported and its surrounding anatomy, and to prevent unwanted displacements or movement of the joint and/or its surrounding anatomy. Because opposing sides of a joint often have slightly different geometries, the size, shape, and location of the first and second support members 203 and 205 may differ from the other. In some embodiments, to the extent that opposing sides of a joint are relatively similar, first and second support members 203 and 205 may be identical. In some embodiments, using identical first and second support members 203 and 205 may reduce manufacturing costs and increase interchangeability, while using different first and second support members 203 and 205 may allow for a better fit.

In one embodiment, as shown in FIGS. 6(a) and 6(b), the first and second support members may be generally planar, and longer in a first direction. In this manner, the support members may reduce unwanted movement of a joint and protect the joint itself from external impacts. Generally planar first and second support members 203 and 205, such as medial support member 202, may also offer the advantage of dissipating any external impacts to the joint over a relatively wider area, and limiting pressure points that may be caused by narrower supports. As illustrated in FIGS. 6(a) and 6(b), medial support member 202 has a relatively wide planar configuration in the area corresponding to the underlying medial malleolus of the ankle joint that is capable of shielding this joint from external impact.

In other embodiments, it is contemplated that first and second support members 203 and 205 may have other suitable configurations including, but not limited to, a variety of polygonal or curved shapes, or even non-planar configurations such as bars, tubes, blocks, or any other shapes capable of supporting and protecting the target joint.

In one embodiment, as shown in FIGS. 6(a) and 6(b), the support member 202 may include ends 216 at the extremities of the support member. The ends 216 may be placed in indirect contact with the portions of the anatomy immediately proximal and distal to the joint to be secured. The contact is generally indirect to the extent that the support member may be housed in a cavity of the main body 100. Placing the ends 216 of first and second support members 203 and 205 in indirect contact with the portions of the anatomy immediately proximal and distal to the joint to be secured may allow the supports to rely on the strength and stability of the larger underlying bone structures surrounding the joint.

For example, a medial support member 202 according to an embodiment of the present invention is shown in FIGS. 6(a) and 6(b). The medial support member 202 may support the medial side of an ankle by slowing and preventing inversion of the ankle. One of the ends 216 of medial support member 202 may indirectly contact a medial side of the lower leg immediately proximal to the ankle joint, while the other end 216 may indirectly contact a medial side of the heel region immediately distal to the ankle joint.

Because of this geometry and orientation, the medial support member 202 may be able to offer resistance against inversion of the ankle.

More specifically, the ability of the medial side of the lower leg, including the underlying tibia bone, and the medial side of the heel region, including the underlying calcaneous bone, to invert towards each other about the ankle joint may be reduced or eliminated by the presence of a support whose ends 216 are indirectly pressed against the surfaces of these anatomical structures, and whose center section is resistant to significant bending.

In one embodiment of the present invention, the need to precisely accommodate the shape of the joint to be supported and its surrounding anatomy may dictate that first and second support members 203 and 205 include protrusions or curved regions in their surfaces to accommodate underlying bones or other structures in a joint. FIGS. 6(a) and 6(b) illustrate one such example, where medial support member 202 includes a curved portion 208 protruding externally from its center to more precisely accommodate the shape of the medial malleolus of the ankle. In other embodiments, similar protrusions or curved members may be employed to accommodate a variety of bones or other anatomical structures.

In an embodiment of the present invention, first and second support members 203 and 205 may be custom made for a particular wearer of a joint support device 10 based on information or data obtained from the wearer. The dimensions of a wearer's joint and surrounding anatomy, as well as any other requirements or preferences of the wearer, may be recorded by the wearer or another individual and provided to a manufacturer of first and second support members 203 and 205. Conventional measuring techniques including, but not limited to, rulers, measuring tapes, two or three dimensional scanners, pressure sensors, photos, videos, or other similar means may be used to obtain fit-related parameters. Manufacturing techniques for custom made inserts might include machining, thermo-forming, or pressing in order to realize the desired parameters. The customization process may be adapted to provide support members that may reduce or eliminate unwanted pressure points, may offer more natural bending characteristics similar to those of the underlying joint, and may increase overall design aesthetics.

In one embodiment, first and second support members 203 and 205 may include one or more structural features to vary their performance and/or appearance. In one embodiment, as shown in FIGS. 6(a) and 6(b), the medial support member 202 may include a series of grooves 206 running in a proximal-distal direction along the length of the medial support member 202. The grooves 206 may be oriented so as to impart additional strength in a unidirectional orientation. In this manner, for example, the joint support device 10 may provide resistance against inversion or eversion of the ankle, yet still allow the ankle to flex and extend while running or jumping. Other structural features including, but not limited to, ridges, bumps, dimples, or holes, are also considered to be within the scope of the present invention.

In an embodiment of the present invention, as shown in FIGS. 1-5, first and second support members 203 and 205 are disposed in first and second cavities 211 and 213. As described above, the desired locations of the support member and their corresponding cavities (i.e. first portion 124 and second portion 126 of main body 100, respectively) will vary depending on the anatomy of the particular joint and the particular type of joint displacement and/or injury that is desired to be avoided.

The first and second cavities 211 and 213 act as receptacles to house the first and second support members 203 and 205 within main body 100. First and second cavities 211 and 213 are generally defined as the space between an exterior surface 110 and an interior surface 108 of the main body 100. In one embodiment, the first and second support members 203 and 205 may be at least partially housed by first and second cavities 211 and 213, respectively, but not entirely contained therein. In one embodiment, the support members may be entirely contained within their respective cavities.

In one embodiment of the present invention, first and second cavities 211 and 213 may be sealed such that the support members are not removable. In another embodiment of the present invention, first and second cavities 211 and 213 are left open to the extent that after manufacture of the joint support device 10 is complete, it is still possible for first and second support members 203 and 205, or other elements, to be removed from or added to the cavities. In this manner, the first and second support members 203 and 205 may be removable and/or replaceable to the extent that interchangeability of support members or insertion of custom made support members, as described above, is desired.

Figure 7:
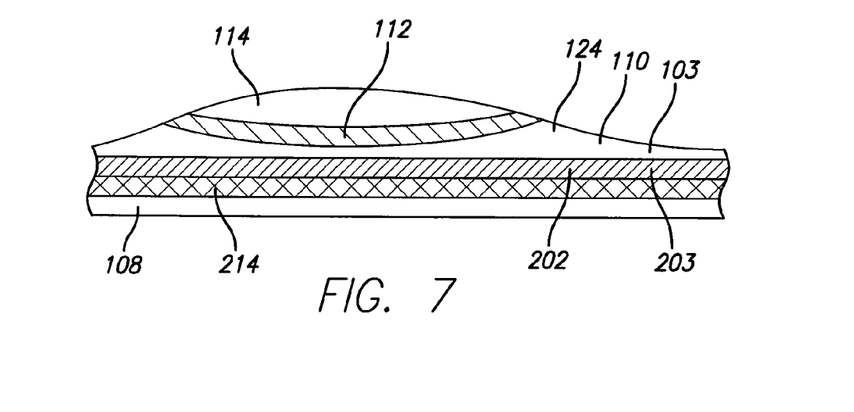
FIG. 7 is a cross-sectional view of a medial portion of a main body of a support device for an ankle according to an embodiment of the present invention.

As illustrated by FIG. 7, the first and second cavities 211 and 213 may also include additional cushioning or padding 214 along with the first and second support members 203 and 205. The padding 214 may be disposed between the first support member 203 and an interior surface 108 of the first portion 124 of the main body 100 and/or between the second support member 205 and an interior surface 108 of the second portion 126 of the main body 100. The padding 214 may provide a better, more comfortable fit to the wearer, and may do so without adding significant weight to the overall design. Additionally, the padding 214 may help disperse impact forces.

In one embodiment of the present invention, as shown in FIGS. 1-4, the exterior surface 110 of the main body 100 forming the exterior portions of the first and second cavities 211 and 213 may include one or more windows 114. The windows 114 may allow at least a portion of the first and second support members 203 and 205 to be at least partially visible from the outside of the main body 100. In one embodiment of the present invention, the windows 114 may be made of a mesh material. However, it is contemplated that other types of windows 114, such as translucent or transparent solid surfaces, are considered to be within the scope and spirit of the present invention.

Moreover, the windows 114 may be surrounded by a frame 112. The frames 112 may hold the windows in position on the exterior surface 110 of the main body 100, or they may merely be disposed adjacent to the windows. The frames 112 and windows 114 may be secured to one another and/or the main body 100 by glue, stitching, or other conventional means. Moreover, multiple separate windows 114 may be present near each of the support members.

Because the windows 114 may allow at least a portion of the support members to be seen from the outside of the main body, wearers of the support may choose to further customize the support by, for example, placing support members bearing their favorite color, favorite team logo or team colors, or other personalized indicia within the cavities. The user may also be able to select various levels of support, material compositions, or a variety of other parameters.

To the extent that both medial and lateral support members 202 and 204 disposed in medial and lateral cavities 210 and 212 have been described for a particular embodiment of the present invention, it will be apparent to one of ordinary skill in the art that, under certain circumstances, it may be desirable to include a support and corresponding cavity on only one side of the described support device 10. In other words, a joint support device 10 having only one support member on one side is considered to be within the scope and spirit of the present invention.

Figure 5:
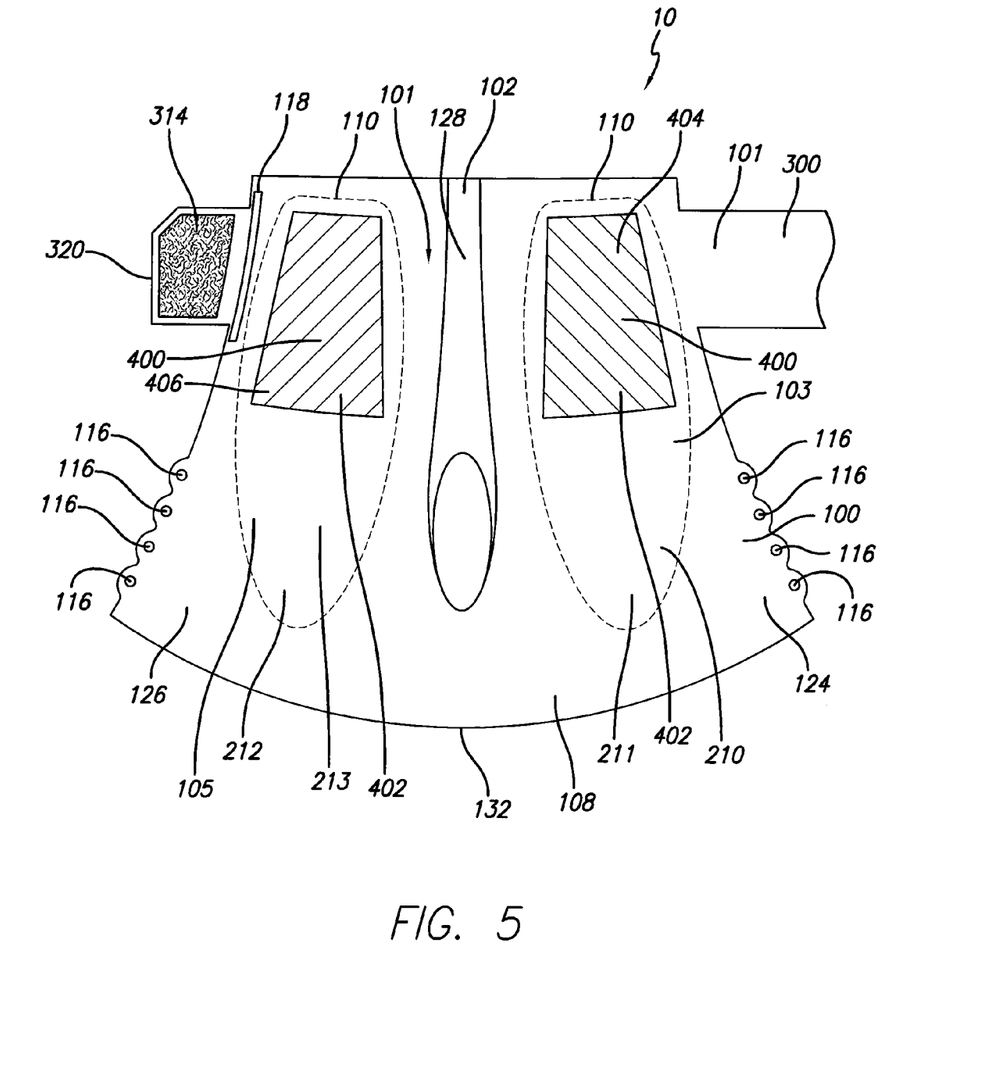
FIG. 5 is a front view of an interior surface of a support device for an ankle wherein a flexible front portion has been removed, a portion of a strap has been removed, and the joint support has been opened up, according to an embodiment of the present invention.

In an embodiment of the present invention, as best shown by FIG. 5, a strap 300 may be disposed on a portion 101 of the main body 100 that is located proximal to the joint to be supported. When coupled to the main body 100, the strap 300 may secure the proximal portion 101 of the main body 100 to the joint and its immediately proximal anatomy. In some instances, the strap 300 may also act to inhibit rotation of the joint about an axis running approximately parallel to major bone structure of the anatomy immediately proximal to the supported joint. Additional straps may also be disposed on other portions of the main body 100, such as a distal portion.

In certain configurations, as best illustrated by FIGS. 1 and 2, the strap 300 may also overlap a portion of the external surface 110 of main body 100 which covers a proximal end 216 of first or second support member 203 or 205. In this case, the strap 300 may also act to strengthen and secure the first or second support member 203 or 205 and its surrounding main body 100 to the joint to be secured. When the first or second support members 203 and 205 are secured in this manner, the overall efficacy of the joint support device 10 may be increased.

In one embodiment of the present invention, the strap 300 may be fixedly attached to a proximal portion 101 of a main body 100 at the strap's fixed end 306, and releasably attached at the strap's free end 308. The strap 300 may be capable of being wrapped around the main body 100 and the joint to be secured, or its surrounding anatomy.

Fastening means 318, such as, for example, hook and pile fasteners, secure the strap 300 to the main body 100. Other suitable fastening means 318, including, but not limited to, snaps, hook, clasps, buttons, or zippers may be used.

In one embodiment, the strap 300 may be capable of being wrapped around the proximal portion 101 of the main body 100, including the underlying anatomy immediately proximal to the secured joint. For example, for a joint support designed for an ankle, the strap 300 may be capable of wrapping at least partially around the proximal portion 101 of the main body 100 while a portion of the wearer's lower leg immediately proximal to the ankle is included within the bounds of the proximal portion 101 of the main body 100.

In one embodiment, as shown in FIGS. 1-5, 8($a$), and 8($b$), the strap 300 may have a two-zone fastening system for securing the strap 300 to the main body 100. The two zones may be created by having two separate fastening means 318 located on the same strap. One of the fastening means 318 may be capable of creating tension around and compression into the main body 100 along the length of the strap 300, from the point where the strap 300 is fixedly connected to the main body 100 to the point where the first of the fastening means 318 is connected to the main body 100. The other of the fastening means 318 may be capable of creating tension around and compression into the main body 100 along the length of the strap 300 from the point where the first of the fastening means 318 is connected to the main body 100 to the point where the second of the fastening means 318 is connected to the main body 100.

Figure 8A:
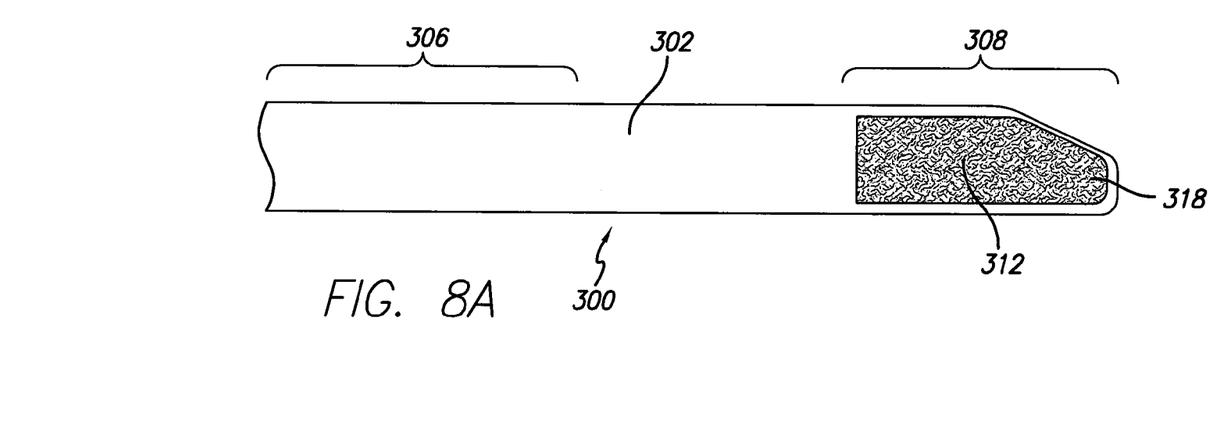
Figure 8B:
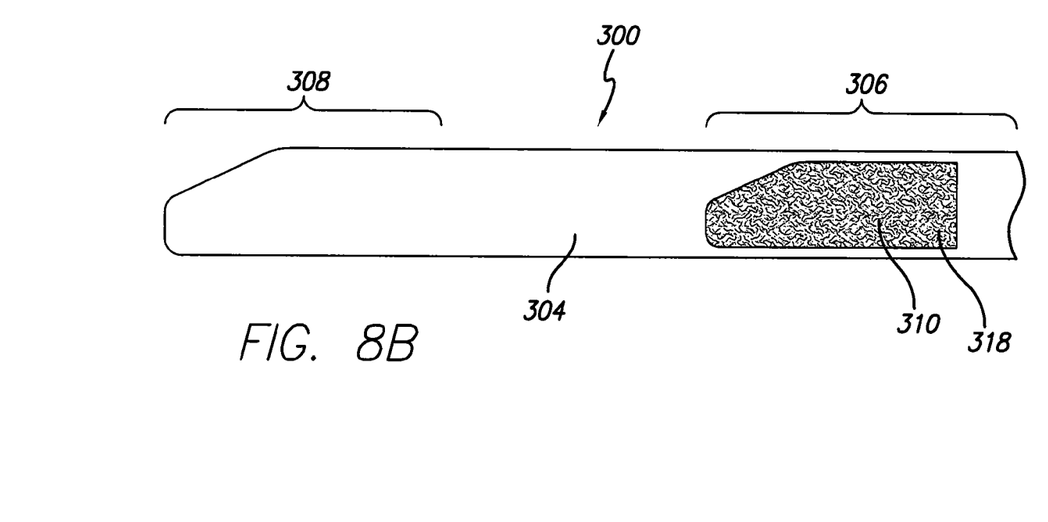

In one embodiment, as shown in FIGS. 8($a$) and 8($b$), the strap 300 includes an interior strap surface 302 and an exterior strap surface 304. The exterior strap surface 304 may have a exterior strap fastening means 310 located near the fixed end 306 of the strap 300. The interior strap surface 302 may have a interior strap fastening means 312 located near the free end 308 of the strap 300.

Correspondingly, as shown in FIGS. 4 and 5, the main body 100 may include a tab 320 extending from a proximal portion 101 of the main body 100. The tab 320 has a interior tab fastening means 314 on its interior surface and a exterior tab fastening means 316 on its exterior surface. The area of the proximal portion 101 of the main body 100 closest to the point where the tab 320 branches off may also include a strap slot 118. The strap slot 118 is an aperture in the main body 100 capable of allowing a portion of the strap 300 to pass through it. The main body 100 may also include additional strap guides 120, as shown in FIGS. 1-3, for guiding the strap 300 as it wraps around the joint.

To tighten the strap 300 around the joint to be supported and its immediately surrounding anatomy, the strap 300 may be wrapped around the proximal portion of the main body 100 while the exterior and interior strap fastening means 310 and 312 are connected to the interior and exterior tab fastening means 314 and 316.

For example, operation of an embodiment of the present invention designed to support a right ankle joint and incorporating such a strap configuration as shown in FIGS. 1-5, 8(*a*), and 8(*b*) will now be described. In this embodiment, with the interior strap surface 302 facing inward towards the ankle joint, the free end 308 of the strap 300 may be wrapped around the front of the ankle joint and threaded through strap slot 118. As the strap 300 is pulled taught through the strap slot 118, the exterior strap surface 304 bearing the exterior strap fastening means will generally end up in a forward, lateral position above the ankle joint. Some portion of the exterior strap fastening means 310 may be pulled through the strap slot 118. While the strap 300 is pulled taught, the tab 320 may be folded down so that the interior tab fastening means 314 engages with a portion of exterior strap fastening means 310. Thus, the strap 300 may create tension around and compression into the front side of the main body 100 and underlying ankle joint.

The strap 300 may again be pulled taught, this time around the proximal rear portion 102 of main body 100. The free end 308 of the strap 300 may be threaded through a rear strap slot 118 to guide it around the proximal rear portion 102 of main body 100. In some embodiments, there may be an additional advantage to the direction the strap is wrapped around the ankle. By wrapping from the medial to lateral side, a wearer may be able to achieve better mechanical advantage. This is contrary to the natural tendency to wrap in the opposite direction.

The strap 300 may then be wrapped around the proximal medial portion 103 of the main body 100, and then may finally be pulled taught so that it wraps back around the front of the ankle joint, so that a portion of the free end 308 of the strap 300 overlaps a portion of the fixed end 306. At this point, the interior strap fastening means 312 may be engaged with the exterior strap fastening means 310. Because tab 320 was folded over a portion of exterior strap fastening means 310, exposing exterior tab fastening means 316 to the exterior of the support, a portion of interior strap fastening means 312 may also be engaged with exterior tab fastening means 316. Thus, the strap may create tension around and compression into the rear side of the main body 100 and underlying ankle joint.

In the exemplary embodiment employing the two-zone fastening system described above, two separate zones of tension and compression are created. This may have the effect of more evenly distributing the tension and compression around the circumference of the joint or its surrounding anatomy. Such an arrangement may thus reduce or eliminate clamping or other sources of discomfort that may arise in a traditional strap fastening arrangement.

In an embodiment of the present invention, as shown in FIG. 5, one or more proprioceptive members 400 may be disposed on interior surfaces 108 of the main body 100. When coupled to the main body 100, the proprioceptive members 400 may function to selectively stimulate the body's proprioceptive response, increasing tension in specific muscles to assist in resisting or slowing the rate of unwanted joint motions. Accordingly, the proprioceptive members 400 may work in conjunction with the initial resistance provided by other elements of the joint support (such as first and second support members 203 and 205) to combine to reduce the probability of injury.

Just underneath the surface of the skin, muscles, ligaments, and tendons of the body are receptors known as proprioceptive receptors. As will be apparent to those of ordinary skill in the art, proprioceptive receptors are capable of initiating increased tension in their associated muscles after sensing relative motion between, or other tactile sensations on, portions of the skin in the vicinity of these receptors.

In order to increase the sensitivity for activating these receptors while wearing a joint support device, proprioceptive members 400 having a relatively high coefficient of friction with respect to the skin may be placed on an interior surface 108 of the main body 100 of the joint support device 10 in contact with the skin. Because of these highly frictional elements, perturbations of the surrounding support device 10 due to joint movements are more likely to be transmitted directly to the surface of the skin around joint to be supported.

In one embodiment of the present invention, the proprioceptive members 400 may be made of a TPU. However, it is contemplated that other suitable materials that have a higher coefficient of friction with respect to the skin than the majority of the other materials making up the interior surface 108 of main body 100, including, but not limited to, leathers, rubbers, plastics, or composites, may be used.

Proprioceptive members 400 may be formed in a variety of shapes, sizes, and patterns. In one embodiment of the present invention, the proprioceptive members 400 may be substantially planar polygonal sheets of TPU. In another embodiment of the present invention, the proprioceptive members 400 may be a series of closely spaced TPU ribs. The ribs may be adapted to be substantial enough to generate enough friction with the skin, yet not so large that they cause discomfort, which could dissuade a wearer from using the joint support.

The proprioceptive members 400 may be attached to the interior surface 108 of main body 100 by stitching, gluing, injection molding, painting, or any other suitable means.

The number and location of the proprioceptive members 400 determines which receptors will be activated (and, thus, which muscles will be tensed). When the proprioceptive members 400 are properly placed, the appropriate muscles will be activated to best counteract a given unwanted joint movement. In some instances, a single proprioceptive member may be sufficient to initiate the required reaction. In other instances, a plurality of proprioceptive members may yield better results.

In one embodiment of the present invention designed to support a right ankle joint, as shown in FIG. 5, two separate proprioceptive members 400 may be employed. In this embodiment, proprioceptive members 400 may be located in the proximal medial portion 101, 103 above the ankle and the proximal lateral portion 101, 105 of the interior surface 108 of the main body 100 above the ankle. The proprioceptive members located in the medial and lateral portions 103 and 105 are positioned to activate the Peroneus, Triceps Surae, and Tibialis Anterior muscles, respectively.

In an embodiment of the present invention, the main body 100 may be coupled to a bladder capable of containing gasses or liquids. The bladder may be located anywhere throughout the main body 100 of the joint support device 10, or the bladder may be externally mountable to the main body 100. The bladder may be located on an interior surface 108 or exterior surface 110 of the main body, or in between interior and exterior surfaces of 108 and 110 of the main body 100. In embodiments in which the bladder is located between the interior and exterior surfaces 108 and 110, the bladder may be located within the first or second cavities 211 or 213, or it may be located outside of them. In the case where the bladder is located within a first or second cavity 211 or 213, the bladder itself may serve as the first or second support 203 or 205. In one embodiment of the present invention, the bladder may be capable of being filled with a liquid and then frozen, thus allowing the bladder to act as a cooling element or ice pack. The bladder may also be heated or contain heating elements to warm muscles prior to use or to help reduce swelling from an injury.

The bladder may be made of any suitable substance capable of retaining gasses or liquids, including, but not limited to, rubbers or plastics. The bladder may be permanently contained within main body 100, or may be removable and, thus, replaceable. The bladder may be pre-filled with a gas or liquid before inclusion in the main body 100, or it may be fillable or refillable at a later point in time. In the case where the bladder may be filled, the bladder may include a nozzle, orifice, or other suitable filling element. The bladder may further include a pump to facilitate filling. A single bladder or a plurality of bladders may be included in main body 100.

Figure 11:
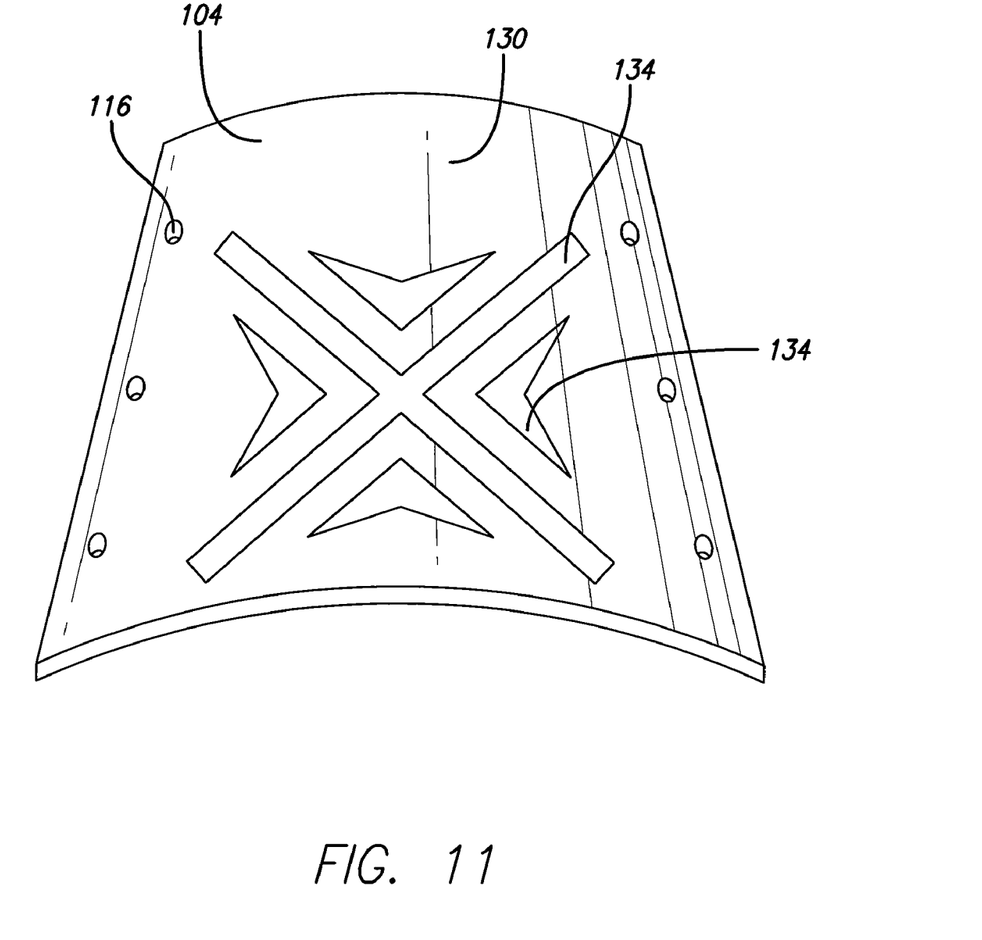
FIG. 11 is a front view of a portion of a main body of a joint support device according to an embodiment of the present invention.

In an embodiment of the present invention, one or more compression bands 134 may be added to the main body 100 of a joint support device 10 to aid in joint stabilization and support. The compression bands 134 may be included on an interior surface 108 or an exterior surface 110 of the main body. The compression bands 134 are capable of enabling the main body 100 of the joint support to better support the natural flexing, expansion, and contractions of the joint, its immediately surrounding anatomy, and underlying muscles. In one embodiment of the present invention, the compression bands 134 are highly elastic TPU bands. The TPU bands may be laminated, sprayed, printed, glued, or stitched on to the main body 100. As shown in FIG. 11, compression bands 134 may come in a variety of shapes and sizes. In the exemplary embodiment shown in FIG. 11, "X" and "V" shaped TPU compression bands 134 have been laminated onto the surface of the front portion 104 of a support device 10 for an ankle.

Figure 9:
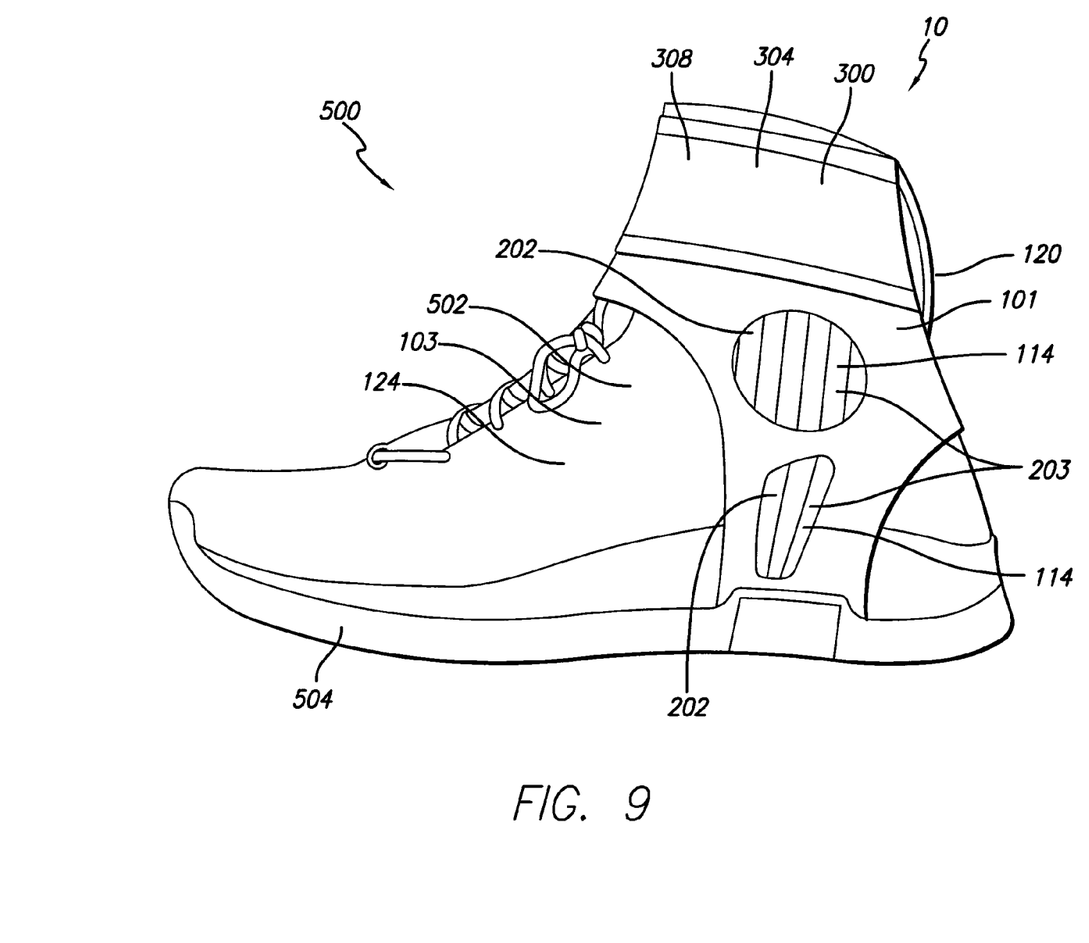
FIG. 9 is a medial view of an article of footwear having an integrated support device for an ankle according to an embodiment of the present invention.

In the embodiments of the present invention designed to support an ankle joint, a support device 10 for an ankle may be worn with a separate article of footwear 500, such as an athletic shoe. Alternatively, a support device 10 for an ankle may be permanently or removably integrated into an article of footwear 500. As shown in FIG. 9, an article of footwear 500 having an integrated support device 10 for an ankle according to one embodiment of the present invention includes an upper 502 disposed around the ankle and a sole 504 disposed below the upper 502. A medial cavity 210 containing a medial support member 202 is disposed in a medial portion 103 of the upper 502. On the lateral side (not shown in FIG. 9) a lateral cavity 212 containing a lateral support member 204 is disposed opposite of the medial cavity 210 in a lateral portion 105 of the upper 502. A strap 300 is disposed on a proximal portion 101 of upper 502, and one or more proprioceptive members 400 (not shown in FIG. 9) are disposed on an interior surface 108 of the upper 502. The structural features and functionality of the article of footwear 500 having an integrated support device 10 for an ankle are similar to the structural features and functionality of some embodiments of a plain joint support device 10 according to the present invention.

In one embodiment, the upper 502 is capable of serving many of the same functions as the main body 100 of joint support devices 10 according to various embodiments of the present invention. In one embodiment, a separate main body 100 may be integrated with an upper 500. In another embodiment of the present invention, the upper 502 or main body 100 may incorporate a fluid-fillable bladder system to improve fit and comfort. As will be appreciated to those of ordinary skill in the art, the fluid-fillable bladder system may include a bladder that may be operatively connected to a pump as disclosed in, for example, U.S. Pat. No. 6,785,985 to Marvin et al., the disclosure of which is incorporated herein by reference thereto.

In one embodiment of the present invention, the joint support device 10 may include an "intelligent" joint support system 600, such that an adjustable support control element 608 may be dynamically manipulated to provide the desired level of support, depending on the needs and/or environment of the wearer.

Figure 10:
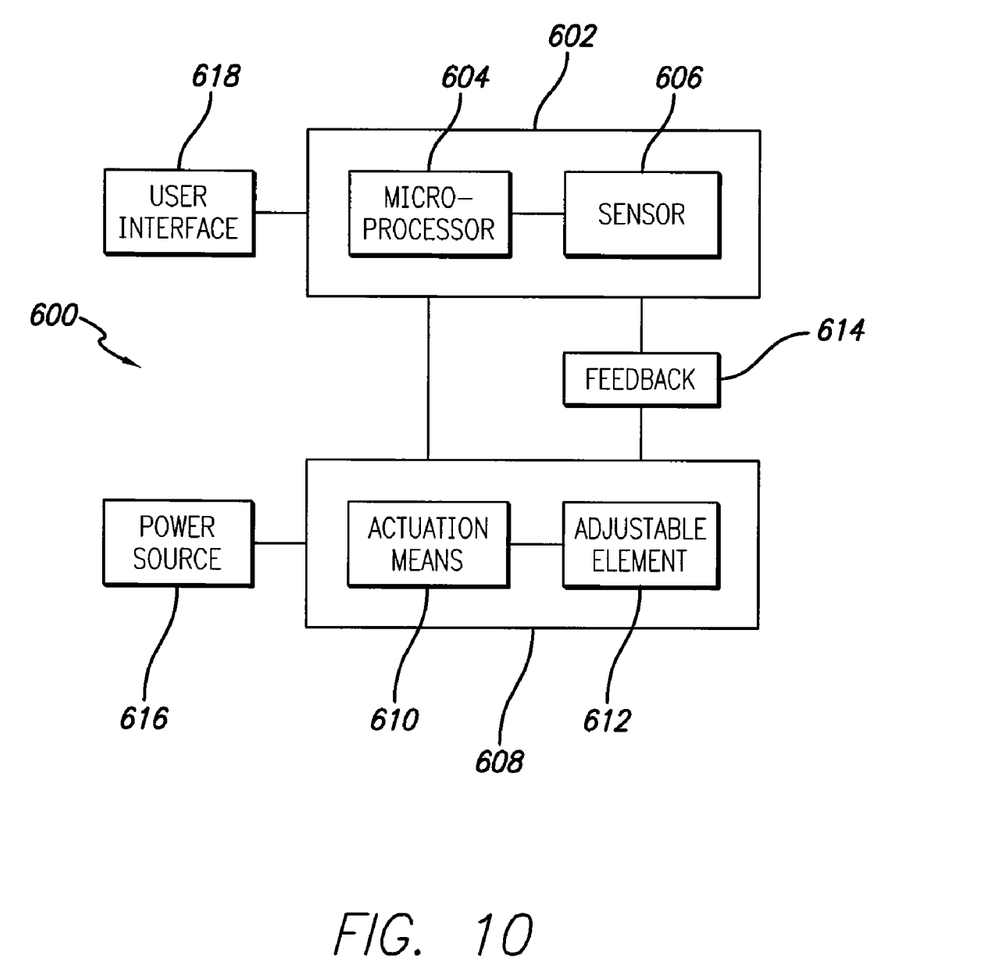
FIG. 10 is a block diagram of an intelligent joint support device according to an embodiment of the present invention.

In one embodiment, as shown in FIG. 10, a control system 602 including a microprocessor 604 and a sensor 606 may be operatively connected to a support control element 608 disposed in the joint support device 10. The sensor 606 may be located, for example, in the cavities 211 or 213, the lower portion 132, or other suitable portion of the support device 10 in order to provide data related to the wearer or the support itself. Sensors 606 including, but not limited to, a pressure sensor, a force transducer, a hall effect sensor, a strain gauge, a piezoelectric element, a load cell, a proximity sensor, an optical sensor, an accelerometer, a hall element or sensor, a capacitance sensor, an inductance sensor, an ultrasonic transducer and receiver, a radio frequency emitter and receiver, a magneto-resistive element, or a giant magneto-resistive element, may be used. The sensor 606 may detect a value for one or more performance conditions, such as, for example, torsion forces or compression forces acting on the support device 10.

As the sensor 606 detects a value for the monitored condition, instructions stored in the microprocessor 604 may indicate the desired reaction to the condition by the support control element 608. For example, if the sensor 606 detects a joint position that indicates that inversion of an ankle is occurring, the microprocessor 604 may determine that an increase in resistance against an inward rolling of the bottom of the foot toward the medial plane is required.

The microprocessor 604 may then communicate instructions to a support control element actuation means 610, which, in turn, actuates an adjustable element 612 in the support control element 608 such that support is increased. The actuation means 610 may comprise mechanical, electro-mechanical, hydraulic, or other suitable means for actuating the adjustable element 612. The adjustable element may be a first or second support member 203 or 205, a bladder, a strap 300, or other suitable components of the support device 10.

A feedback loop 614 may update the control system 602 with information about the current state of the support control element 608, and the performance conditions of the joint support device 10 may be continually monitored.

In one embodiment, a power source 616, such as, for example, a battery may be operatively connected to the intelligent joint support system 600. The power source 616 may be disposed in or on the joint support device 10, may be removable from the joint support device 10, or may be an external power source that selectively connects to the intelligent joint support system 600. In one embodiment, a user interface 618 may be operatively connected to the intelligent joint support system 600. The user interface 618 may be used to select a desired operation mode (e.g., a running mode with less resistance or a basketball mode with more resistance), or input desired instructions to the microprocessor 604. The user interface 618 may also provide output of certain data or conditions to the user. As will be appreciated to those of ordinary skill in the art, other features of an "intelligent" support system may be incorporated, including those disclosed in, for example, U.S. Pat. No. 7,188,439 to DiBenedetto et al., the disclosure of which is incorporated herein by reference thereto.

The breadth and scope of the present invention should not be limited by any of the above-described exemplary embodiments, but should be defined only in accordance with the following claims and their equivalents.

What is claimed is:

1. A support device for an ankle, comprising:
   a main body having a medial portion and a lateral portion disposed about the ankle, and an interior surface;
   at least one of a medial support member disposed in a cavity in the medial portion of said main body and a lateral support member disposed in a cavity in the lateral portion of said main body;
   a strap disposed on a proximal portion of said main body, said strap having fastening means adapted to create a first level of pressure in the front of the lower leg immediately proximal to the ankle and a second level of pressure in the rear of the lower leg immediately proximal to the ankle; and one or more proprioceptive members disposed on the interior surface of said main body.

2. The support device for an ankle of claim 1, wherein said main body further comprises a flexible front portion and a flexible rear portion disposed opposite of one another, and wherein edges of the front portion and the rear portion are coupled to edges of the medial portion and the lateral portion.

3. The support device for an ankle of claim 2, wherein the medial portion and the lateral portion each have an expandable portion disposed therein.

4. The support device for an ankle of claim 1, wherein a part of at least one of said medial support member and said lateral support member is at least partially visible through an exterior surface of said main body.

5. The support device for an ankle of claim 1, wherein at least one of said medial support member and said lateral support member is removable from its cavity.

6. The support device for an ankle of claim 1, further comprising a plurality of grooves disposed on at least one of said medial support member and said lateral support member.

7. The support device for an ankle of claim 1, wherein at least one of said medial support member and said lateral support member is formed so as to accommodate the shape of the ankle joint underlying said main body.

8. The support device for an ankle of claim 7, wherein at least one of said medial support member and said lateral support member is custom made for a wearer of the support device for an ankle based on information obtained from the wearer.

9. The support device for an ankle of claim 1, wherein said main body is coupled to a fluid-fillable bladder.

10. The support device for an ankle of claim 1, further comprising padding disposed between at least one of said medial support member and said lateral support member and the underlying ankle joint.

11. The support device for an ankle of claim 1, further comprising one or more compression bands disposed on a surface of said main body.

12. The support device for an ankle of claim 1, further comprising a sensor for detecting a value.

13. The support device for an ankle of claim 12, wherein the value obtained from said sensor is processed by a microprocessor.

14. The support device for an ankle of claim 12, wherein said sensor is coupled to an adjustable support control element which is capable of being dynamically manipulated.

15. The support device for an ankle of claim 1, wherein the fastening means of the strap comprise exterior and interior strap fastening means disposed on opposite sides of said strap and said main body having fastening means adapted to operatively connect with said exterior and interior strap fastening means.

16. The support device for an ankle of claim 1, wherein said one or more proprioceptive members are disposed in at least one of a medial portion of the interior surface of said main body, and a lateral portion of the interior surface of said main body.

17. The support device for an ankle of claim 1, wherein said one or more proprioceptive members comprise a plurality of TPU ribs.

18. A support device for an ankle, comprising:
a main body having a medial portion and a lateral portion disposed about the ankle, and an interior surface;
at least one of a medial support member disposed in a cavity in the medial portion of said main body and a lateral support member disposed in a cavity in the lateral portion of said main body;
a strap disposed on a proximal portion of said main body; and
proprioceptive members disposed on a medial portion of the interior surface of said main body above the ankle and on a lateral portion of the interior surface of said main body above the ankle.

19. The support device for an ankle of claim 18, wherein at least one of said medial support member and said lateral support member is formed so as to accommodate a protrusion of the malleolus of the ankle joint.

20. The support device for an ankle of claim 18, wherein said strap has fastening means capable of creating different levels of pressure in the front and the rear parts of the lower leg immediately proximal to the ankle joint.

21. An article of footwear having an integrated support device for an ankle comprising:
an upper having a medial portion and a lateral portion disposed about the ankle;
a sole disposed below said upper;
at least one of a medial support member disposed in a cavity in the medial portion of said upper and a lateral support member disposed in a cavity in the lateral portion of said upper;
a strap disposed on a proximal portion of said upper; and
one or more proprioceptive members disposed on an interior surface of said upper.

22. The article of footwear of claim 21, wherein said strap has fastening means capable of creating different levels of pressure in the front and the rear parts of the lower leg immediately proximal to the ankle joint.

23. The article of footwear of claim 21, wherein said one or more proprioceptive members are disposed in a proximal portion of the interior surface of said upper.

24. A support device for an ankle, comprising:
a main body having an interior surface, said main body comprising:
a medial portion having a medial cavity formed therein,
a lateral portion having a lateral cavity formed therein, and
a tab extending from the lateral portion, said tab having fastening means disposed on an interior surface and an exterior surface of the tab;
a medial support member disposed in the medial cavity;
a lateral support member disposed in the lateral cavity;
a strap having a fixed end attached to the medial portion of said main body and a free end, and having exterior fastening means disposed on an exterior surface of said strap at the fixed end and interior fastening means disposed on an interior surface at the free end, wherein the interior tab fastening means is operatively connected to the exterior strap fastening means, and the exterior tab fastening means is operatively connected to the interior strap fastening means; and
proprioceptive members disposed on a medial portion of the interior surface of said main body above the ankle and a lateral portion of the interior surface of said main body above the ankle.

25. The support device for an ankle of claim 24, wherein the interior strap fastening means is also operatively connected to the exterior strap fastening means.

* * * * *